United States Patent [19]

Liu

[11] Patent Number: 5,139,945
[45] Date of Patent: Aug. 18, 1992

[54] THERMOSTABLE ALGINATE LYASE FROM BACILLUS STERAOTHERMOPHILUS

[75] Inventor: Chi-Li Liu, Danbury, Conn.

[73] Assignee: Novo Industri A/S, Bagsvaerd, Denmark

[21] Appl. No.: 245,275

[22] Filed: Sep. 16, 1988

[51] Int. Cl.$^5$ .......................... C12N 9/88; C12N 1/20
[52] U.S. Cl. .................................. 435/232; 435/252.5; 435/832
[58] Field of Search ..................... 435/68.1, 232, 252.5, 435/832

[56] References Cited

PUBLICATIONS

Hansen, J. B. et al. "Distribution of Alginate Lyase Activity among Strains of *Bacillus circulans*", Applied & Environmental Microbiology, vol. 49, No. 4, pp. 1019–1021, 1985.

Wicker-Böckelmann, U. et al., "Alginate Lipase Releases Cell-Bound Lyase from Mucoid Strains of *Pseudomonas aeuginosa*", Zbl. Bakt. Hyg. A 266, pp. 379–389, 1987.

*Primary Examiner*—Douglas W. Robinson
*Assistant Examiner*—Marian C. Knode
*Attorney, Agent, or Firm*—Fidelman & Wolffe

[57] ABSTRACT

A method of producing algal cell wall degrading enzyme by cultivating a thermophilic, bacterial strain of an atypical *Bacillus stearothermophilus* e.g., W36-7-4 (NRRL B-18394) which produces the alginate lyase in a cultivation medium containing sodium alginate and tryptone, then allowing growth to take place to accumulate alginate lyase, and then recovering the enzyme from the fermentation broth. The novel alginate lyase of this invention is useful as a treatment agent for water cooling systems.

2 Claims, 1 Drawing Sheet

THERMOSTABLE ALGINATE LYASE FROM *BACILLUS STERAOTHERMOPHILUS*

The present invention relates to an enzyme useful as an algicide and slime inhibitor and more particularly to a novel alginate lyase which can be used to degrade algae cells and inhibit the growth of slimes.

BACKGROUND OF THE INVENTION

It is well known that uncontrolled growth of microorganisms in a water cooling system (that recirculates the water) can lead to deposit formation which contributes to fouling, corrosion and scale. Slimes can clog piping, hinder heat transfer or otherwise interfere with the proper functioning of a water cooling system. Presence of algae, Chroococcus, Oscillatoria and Chlorococcus in water cooling systems have been identified as causing fouling. In addition, algal slimes seem to become habitat for corrosive bacteria, and perhaps pathogenic bacteria.

Alginic acid (alginate) which is a polysaccharide constitutes the main element of algal cell walls. In some species of algae such as *Fucus distichus*, alginate makes up to 60% of the total cell wall. In addition to algae, some bacteria common in cooling waters, e.g., Pseudomonas spp. produce an extracellular polysaccharide polymer (slime) which results in fouling, formation of gases and protection of corrosive bacteria in water cooling systems. The extracellular polysaccharide polymer (slime) produced by some Pseudomonas spp. has been identified as alginate (L. R. Evans et al., *J. Bacteriol.* 1973, 116:915–924).

Alginate is a copolymer of three main structural blocks, poly-beta-D-mannuronic acid (poly-M), poly-alpha-L-guluronic acid (poly-G), and blocks in which both uronic acids occur in what is believed to be an alternating sequence (poly-MG) (A. Haug et al., *Acta Chem. Scand.* 1967, 21:691–704).

Thus, the action of enzymes such as alginate lyases capable of depolymerizing alginate in the algal cell wall and slimes from Pseudomonas spp. can cause lysis of these organisms and/or increase the susceptibility of these organisms to the chemical biocides which customarily are in water cooling systems. Either result renders these troublesome microorganisms unviable, which consequence is most desirable for best operation of water cooling systems.

The object of this invention is to provide an alginate lyase effective in water cooling systems.

Further objects and advantages of this invention will be apparent from the description thereof which follows.

DISCUSSION OF THE INVENTION

All the alginate lyase enzymes characterized prior to the date hereof, including those from non-bacterial sources, appear to catalyze an eliminase reaction, in which a nonreducing reducing $\Delta$ 4,5 unsaturated bond is produced during cleavage of the uronic acid polymer (I. W. Sutherland. In I. Sutherland (ed.), Surface Carbohydrates of The Prokaryotic Cell. 1977, P. 209–245, Academic press, Inc., London.) Different alginate lyases show a preference for guluronate or mannuronate blocks in the alginate polymer; thus they can be distinguished as guluronidase or mannuronidase (I.W. Davidson et al., *J. Gen. Microbiol.* 1977, 98:223–229).

Numerous bacteria are known to produce enzymes that degrade alginate, but most of these reported alginate lyase-producing bacteria are marine isolates. (R.S. Doubet et al., *Appl. Environ. Microbiol.* 1982, 44:754–756 and V. L. von Riesen. *Appl. Environ. Microbiol.* 1980, 39:92–96). A few characterized alginate lyases have been isolated from bacteria of terrestrial origin: examples include those from *Klebsiella aerogenes* (J. Boyd et al., *Carbohydrate Res.* 1977, 57:163–171) and Bacillus circulans (J.B. Hansen et al., *Appl. Environ. Microbiol.* 1984, 47:704–709). Insofar as the inventor hereof is aware no thermophilic, gram-positive alginate lyase producers have been reported heretofore. The alginate lyase of this invention is produced extracellularly from a thermophilic Bacillus sp.

The inventor's best producer strain (W36-7-4) for the alginate lyase of this invention has been classified taxonomically (by NCIMB) as a strain of *Bacillus stearothermophilus* atypical in growing at pH 5.7. However, the considerable number of other *B. stearothermophilus* strains tested by the inventor hereof do not produce alginate lyase. Tested were ten strains, namely—NRRL B5407, ATCC 12980 -type strain; ATCC 7953, 10149, 31783, 31195, 31196, 31197, 31198 and 31199. Also, other Bacillus sp. strains which were tested do not produce alginate lyase, i.e., *B. coagulans* ATCC 7050; *B. licheniformis* ATCC 14580; *B. subtilis* ATCC 6633; and, *B. cereus* ATCC 11778. Thus, the atypical *B. stearothermophilus* strains found by the inventor hereof in which the alginate lyase is a native extracellular inducible enzyme are atypical also for producing this enzyme.

DETAILED DESCRIPTION OF THE INVENTION

For convenience, the detailed discussion of the alginate lyase of this invention is directed to usage of the lyase as an algalcide and slime inhibitor in water cooling systems (wherein the water recirculates). It should be appreciated that the inventor hereof recognizes and contemplates other uses for their alginate lyase, e.g., extracting cellular components from algae.

For further understanding of this invention, reference is made to the attached drawings wherein:

Figure 2:
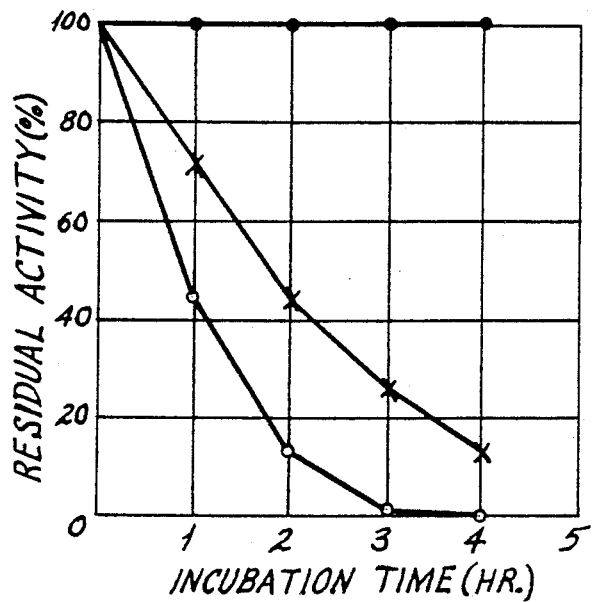
FIG. 2 graphically presents the thermostability of the alginate lyase from the strain W36-7-4 at 60° C. versus known alginate lyases.

As is evidenced in FIG. 2, the alginate lyase of this invention showed superior thermostability over alginate lyases from *Bacillus circulans* (ATCC 15518) and from *Xanthomonas maltophilia* (ATCC 13637). After four hours of heat treatment at 60° C. in the absence of substrate, the enzyme of the invention retained 100% of its original activity whereas the enzyme from *Bacillus circulans* completely lost its original activity and the enzyme from *Xanthomonas maltophilia* lost 88% of its original activity.

The thermal stability characteristics of the alginate lyase, namely that it is stable at 60° C., is a major advantage since 60° C. is at the high end of the usual temperature ranges at which water cooling systems are operated. Thus, the capability of the alginate lyase of this invention for depolymerizing the alginate component of algal cell walls and slimes produced by Pseudomonas spp. in water cooling systems is accompanied by a desirable high level of (thermal) stability in such systems.

When algal cell suspension (obtained from a water cooling tower) was treated with the alginate lyase of the invention, a quantitative release of unsaturated uronic acid moiety was obtained (shown in Table I). The results demonstrate that the alginate component of the algal cell walls are degraded by the alginate lyase. Microscopically, algal cell wall with very small holes can be observed after 60 minutes of enzyme treatment.

Therefore, the present invention comprises also a method for treating water cooling systems which comprises maintaining in the recirculating water concentration of the alginate lyase effective to inhibit proliferation of algae.

It is not only algae that is affected by the alginate lyase. It is evident (see Table III) that the alginate lyase can also depolymerize the alginate polymer produced by *Pseudomonas aeruginosa* (ATCC 9027) which also is a troublesome microbe presence in water cooling systems. Resistance of P. aeruginosa to treatment of the water cooling with biocides is believed due to an alginate-containing envelope. Treating *Pseudomonas aeruginosa* with the alginate lyase of this invention removes the polymer layer and is believed to enhance the susceptibility of the organism to the biocides.

Besides alginate, algal cell walls also contain laminarin, a polysaccharide which can be depolymerized by beta-glucanase. A combination and perhaps synergistic effect on degradation of algal cell walls may be achieved by addition of both a commercially available beta-glucanase (e.g., Ceremix ® 2X L) and the alginate lyase of this invention system as is shown in Table II. Actually Ceremix ® 2X L is a mixture of enzyme activities, notably betaglucanase, alpha-amylase, and protease activities but then commercially available enzyme products often contain substantial side activity enzymes.

Accordingly, the present invention comprises also the method of treating a water cooling system with activity levels and proportions of alginate lyase and a beta-glucanase effective to inhibit growth of algae. A preferred β-glucanase is Ceremix ® which will work advantageously due to the existence of other desirable enzyme activities. Optionally, present with the two enzymes or for that matter instead of the beta-glucanase may be biocide chemicals (e.g., glutaraldehyde, hydrazine) that are non-inhibitory of the enzyme(s).

Advantageously, the alginate lyase of this invention is compatible with the various chemicals which commonly are in current use to treat water cooling systems e.g., EDTA, glutaraldehyde. As indicated in Table IV, the alginate lyase retained 100% of its enzymatic activity after 16 hours incubation with chelating agents, various oxidants and typical corrosion inhibitors. The chemicals tested were at 10 mM final concentration which is about 10-fold higher than the usual dose used in water cooling treatment (100 PPM). It is, therefore, possible to apply the enzyme of the invention in combination with water treatment chemicals, and in particular with the chemicals those conventionally employed heretofore to control microbial problems in water cooling systems.

According to a further aspect of this invention there is provided method for producing the alginate lyase of this invention, a process which is characterized by cultivating an alginate lyase producing strain of the atypical *B. stearothermophilus* exemplified by NRRL B-18394 under aerobic conditions in a nutrient medium containing assimilable sources of carbon, nitrogen, and phosphorus, followed by recovery of the alginate lyase preparation from the fermentation broth.

METHOD OF USE

As has already been indicated the alginate lyase of this invention is well adapted to use in water cooling systems. A solid or liquid (concentrate) form of the alginate lyase is added to the recirculating water of the cooling system in effective amounts. Little advice can be offered as to the minimum effective amount since each water cooling system may be unique, e.g., clean or heavily contaminated water, low or high mineral content in the water (zinc and sodium chloride appear to partially inhibit the enzyme), frequency of dosing with the enzyme, e.g., continuous, weekly, monthly, content of biocide (if any) and whether beta-glucanase e.g., Ceremix ® 2xL will also be present in the cooling system water. A cut and try approach is recommended for ascertaining the least enzyme(s) dosage that is effective. Normally something less than the concentrations hereinafter described as exemplary will suffice.

An effective amount of the alginate lyase of this invention, e.g., 2500 units per liter of water and perhaps less to be treated can be added to tower water. Of course, higher levels of alginate lyase than 2500/1 can also be applied if cost effective. 2.5 ml to 25 ml of Ceremix ® 2xL in combination with the 2500 u/1 of alginate lyase should be quite effective. Commonly used biocides may also be applied together with the alginate lyase (since the enzyme is not inhibited by most of the biocides) at the concentration of 100 PPM which is the level usually recommended (1987 Guide to water treatment chemicals).

THE MICROORGANISM

The microorganism of this invention is an aerobic, bacillus isolate of atypical *Bacillus stearothermophilus*. The best producer strain W36-7-4 (NRRL B-18394) is deposited at the Agricultural Research Culture Collection (NRRL), Peoria, Ill., U.S.A., under the terms of the Budapest Treaty.

Mutants and variants of this strain, W36-7-4 (NRRL B-18394), and like strains of the atypical *Bacillus stearothermophilus*, exemplified by W58-7-12 obtained by methods known in the art, are also within the scope of the invention. Other lyases producing strains of the atypical *Bacillus stearothermophilus* have been found by the inventor hereof and investigated (relatively superficially). The alginate lyase herein exemplified constitutes the preferred mode. Production of the alginate lyase by a transformed host cell is contemplated. The native alginate lyase is an induced enzyme, but may well be made constitutively in mutant, or transformed cells.

Temperature for growth of strain W36-7-4 is 50° C. to 60° C., optimal temperature for growth at 55°-60° C.;poor growth at or above 60° C. Optimal pH for growth strain W36 7-4 is 7.0. No growth occurs at or above pH 8.0.

On nutrient agar slants, mature colonies of strain W36-7-4 are transparent with smooth surfaces.

ASSAY FOR ALGINATE LYASE ACTIVITY

A rudimentary indication of alginate lyase activity is a decrease in viscosity of a 0.5% sodium alginate solution. Quantitative estimates of the alginate lyase reaction have been made by the following methods:

(a) Increase in U.V. absorbance at 230 nm (J. Boyd et al., *Carbohydrate Res.* 1977, 57:163–171). To a 2 ml sodium alginate solution (0.1%, 0.25% or 0.5%) which was made in 10 mM sodium phosphate buffer, pH 7.0 containing 10 mM $MgCl_2$, 0.1 ml of an appropriately diluted enzyme broth was added, and the reaction mixture was incubated at 55° C. for 2 hours with vigorous shaking. At the end of incubation time, the increase in absorbance at 230 nm was measured by use of a spectrophotometer. One unit was defined as the amount of alginate lyase which caused an increase of 0.001 optical density unit (230 nm) per minute at a specified temperature, usually 55° C.

(b) Reducing power. The substrate solution was identical to that above. The substrate solution (2 ml) and enzyme solution (1 ml) were incubated at 55° C. for 2 hrs., and dinitrosalicylate reagent (2 ml) was then added. The reducing power, as mannuronic acid, was determined as described by G. Noelting et al., (G. Noelting et al., *Helv. Chim. Acta.* 1948, 31:286–290). One unit of activity was defined as the amount of enzyme that would liberate reducing power equivalent to 0.123 mg of mannuronic acid under the stated digest-conditions.

(c) Thiobarbituric acid test. The substrate solution was identical to that above. The substrate solution (2 ml) and enzyme solution (1 ml) were incubated at 55° C. for 2 hrs. The yield of unsaturated uronic acid was determined by the periodate/thiobarbituric acid (TBA) procedure of Weissbach and Hurwitz (A. Weissbach et al., *J. Biol. Chem.* 1959, 234:705–709). The unit of enzyme activity was defined as the amount of enzyme needed to liberate the equivalent of 1 μmol per min. of formylpyruvic acid; 0.01 μmol produced an $OD_{549}$ of 0.29 in the assay.

Figure 1A:
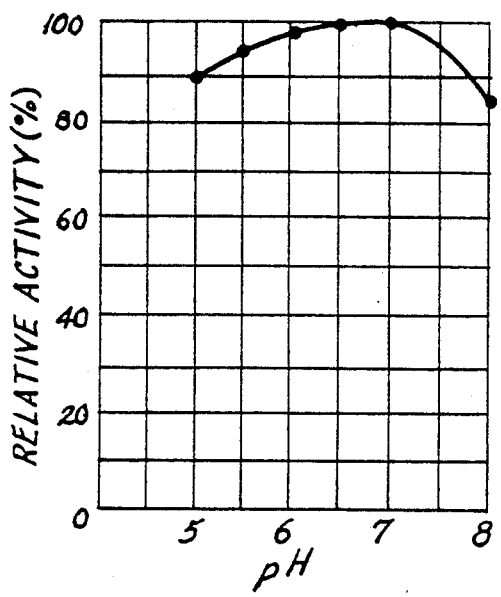
FIG. 1 graphically presents the activity of the alginate lyase from atypical *Bacillus stearothermophilus* strain W36-7-4, (NRRL B-18394) as a function of pH and temperature.
Figure 1B:
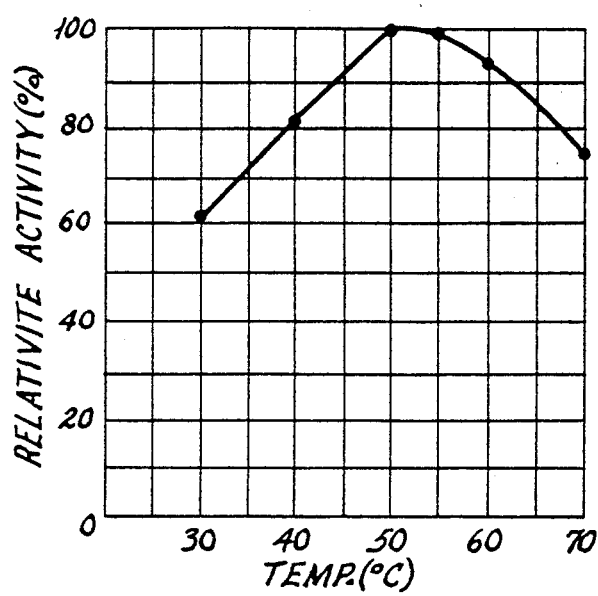

As shown in FIG. 1(a), the optimum activity of the alginate lyase from *Bacillus stearothermophilus* strain W36-7-4 was observed at pH around 7. It is not considered surprising that the alginate lyase enzyme of this invention exhibited the temperature optimum around 50° C. shown in FIG. 1(b) since the microorganism that produces the enzyme is a thermophile.

The alginate lyase from strain W36-7-4 not only showed a high temperature optimum, it also possessed a good thermostability at 60° C. as is shown in FIG. 2. Alginate lyase from *Bacillus circulans* (ATCC 15518) and *Xanthomonas maltophilia* (ATCC 13637) lost 55% and 29% respectively, of the original activity upon one hour heat-treatment at 60° C. The enzyme of the invention retained 100% of its enzymatic activity over four hours of heat treatment.

PREPARATION OF ALGINATE LYASE CONCENTRATE

*Bacillus stearothermophilus* strain W36-7-4 (NRRL B-18394) may be cultivated under aerobic conditions in a nutrient medium containing assimilable carbon and nitrogen together with other essential nutrients. The medium per se is not considered part of this invention and may be formulated in accordance with the principles known in the art for cultivation of *Bacillus stearothermophilus* strains.

If such is desired, sodium alginate may be used as the carbon source as well as the enzyme inducer. The alginate concentration incorporated in the medium may vary widely, e.g., 0.1 to 1% with 0.5% concentration in the solution of the medium usually being suitable.

The nitrogen source in the nutrient medium may be of an organic or inorganic nature. Among the possible organic nitrogen sources, are a number regularly used in fermentation processes (involving the cultivation of bacilli) such as soybean meal, cotton seed meal, peanut meal, corn steep liquor, and yeast extract. In addition, the nutrient medium should also contain the usual trace substances.

Since the atypical *B. stearothermophilus* of the invention is thermophilic, the cultivation is conducted at relatively high temperature (e.g., 55° C.). For cultivation of strain W36-7-4 or a mutant or variant thereof in tank fermentors artificial aeration is recommended. The rate of aeration may be that employed in conventional tank (submerged) fermentation.

After fermentation, the product alginate lyase (which is elaborated extracellularly) may be produced in liquid form by removal of coarse material from the fermentation broth and, then through concentration of the broth by conventional method, e.g., evaporation at low temperature or by ultrafiltration. Finally, preservatives may be added to the concentrate.

According to the invention, alginate lyase can also be prepared by cultivation of a transformant microorganism cell containing a gene encoding for and expressing an alginate lyase derived from a Bacillus strain of the invention, followed by recovery of the enzyme from the culture broth. Said transformed host organism comprises a host cell wherein the gene for the alginate lyase and expression DNA has been inserted by recombinant DNA techniques. Such techniques are known in the art and generally comprise the following steps:

a) providing a suitable recombinant DNA cloning vector comprising DNA-sequences encoding functions facilitating gene expression and a DNA-sequence encoding the Bacillus alginate lyase;

b) transforming a suitable host organism with the cloning vector from step a); and then c) culturing the transformed host in a suitable culture medium and recovering the alginate lyase from the culture medium.

Preferred host organisms are strains of Bacillus, especially of *Bacillus subtilus*.

ENZYME PREPARATION

Solid enzyme preparations, when such is desired may be prepared from the purified and/or concentrated fermentation broth by precipitation with salts such as $Na_2SO_4$ or with water miscible solvents such as ethanol or acetone. Removal of all the water in the fermentation broth by suitable drying methods such as spray drying may also be employed. The activity of crude alginate lyase preparations so obtained from cultivation of NRRL B-18394 is usually about 5000 units/g of powder.

Preferred alginate lyase preparation of the invention are, of course, in forms suitable for movement in commerce as a water cooling treatment agent, such as a non-dusting granulate, a stabilized liquid or a protected enzyme.

Non-dusting enzyme granulates are well known in the art and, for example, may be produced according to NL 167,993 (NOVO), U.S. Pat. Nos. 4,106,991 (NOVO) or 4,661,452 (NOVO) and optionally the granulate may be coated according to known in the art practices.

A liquid alginate lyase preparation may be stabilized, e.g., by addition of propylene glycol, other polyols, sugars, sugar alcohols and boric acid. Other enzyme stabilizers known in the art may be employed.

The following Examples describe preparation of the enzyme, characterization thereof and exemplary uses thereof.

EXAMPLE 1

*Bacillus stearothermophilus* strain W36-7-4 (NRRL B-18394) was cultivated at 55° C. on a rotary shaking table (250 rpm) in 250 ml triple-baffled Erlenmeyer flasks containing 50 ml of medium of the following composition:

Composition of the medium in grams per liter:
Tryptone: 1.0
$(NH_4)_2SO_4$: 2.0
$KH_2PO_4$: 1.3
$Na_2HPO_4$: 3.5
$MgCl_2 \cdot 2H_2O$: 0.2
$CaCl_2 \cdot 2H_2O$: 0.2
Sodium alginate: 5.0

No pH adjustment of the medium was necessary. After 30 hours incubation, the alginate lyase activity of the broth was determined by using the U.V. absorbance assay as described above. The alginate lyase activity of the W36-7-4 broth was 21 U/ml with 0.1% sodium alginate as the substrate.

EXAMPLE 2

The pH-activity and temperature-activity curves of crude alginate lyase from *Bacillus stearothermophilus* strain W36-7-4 (NRRL B-18394).

Alginate lyase activity (increase in optical density at 230 nm) at 55° C. was monitored with sodium alginate as the substrate. Constant amounts of substrate, enzyme and $MgCl_2$ (10 mM) were present in all reactions. Citrate-phosphate buffer was used between pH 5.0 and 6.5 and phosphate buffer was used between pH 6.0 and 8.0. The maximum activity was observed around pH 7.0, see FIG. 1a.

The temperature-activity curve was constructed by monitoring alginate lyase activity of this invention at temperature between 30° C. to 70° C. in 10 mM phosphate buffer, pH 7.0 containing 10 mM $MgCl_2$. The maximum activity was observed around 50° C., see FIG. 1b.

EXAMPLE 3

A comparison of thermostability of alginate lyases from *Bacillus stearothermophilus* strain W36-7-4(●), *Bacillus circulans* (ATCC 15518) (0) and *Xanthomonas maltophilia* (ATCC 13637) (X).

Each 2.0 ml of a crude enzyme solution was heat-treated at 60° C. using the same buffer as employed in the text. The heat-treatment lasted for 4 hours. Then, the solution was immediately cooled to room temperature in cold water bath and the residual enzyme activities were measured using sodium alginate as the substrate. After 4 hours incubation, alginate lyase from strain W36-7-4 retained 100% of its original activity whereas the enzyme from *Bacillus circulans* and *Xanthomonas maltophilia* lost 100% and 88% of its original activity respectively, see FIG. 2.

EXAMPLE 4

The release of unsaturated uronic acid moiety from the alginate component of algal cell walls by alginate lyase from *Bacillus stearothermophilus* strain W36-7-4.

2.0 ml of algal suspensions obtained from a factory cooling water tower buffered to final concentration of 10 mM phosphate buffer, pH 7.0 was treated with different levels of alginate lyase from strain W36-7-4 at 37° C. The liberation of 4-deoxy-L-erythro-hex-5-ulosuronic acid was monitored through measuring the U.V. absorption at 230 nm; the results obtained are tabulated in Table 1.

TABLE 1

| | $\Delta OD_{230\ nm}$ | | |
|---|---|---|---|
| Incubation time | 0 mg Enzyme | 3 mg Enzyme* | 5 mg Enzyme |
| 3.5 hr | 0 | 0 | 0.7 |
| 15 hr | 0.05 | 0.4 | 1.30 |
| 22.5 hr | 0 | 1.25 | 3.05 |

*Enzyme was added as crude enzyme lyophils of about 5000 U/g.

EXAMPLE 5

The conbinational affect of beta-glucanase, i.e. Ceremix ® 2X L, and the alginate lyase from *Bacillus stearothermophilus* strain W36-7-4 on the digestion of alginate component in algal cell walls.

The algal suspensions were the same as used in Example 4. The alginate lyase was dosed in at the level of 5 mg of the crude enzyme lyophil per 2 ml of algal cell suspension and the NOVO commercial product Ceremix ® 2X L was added at 50 ul per testing sample. The digestion was monitored as described in Example 4.

A synergistic effect of Ceremix ® 2X L and alginate lyase on the digestion of algal cell walls appears to be evidenced, the data being set forth in Table II.

TABLE II

| | $\Delta OD_{230\ nm}$ | | | |
|---|---|---|---|---|
| Incubation time | No Enzyme | 5 mg alginate lyase Alone | 50 ul Ceremix ® 2X L Alone | 5 mg alginate lyase + 50 ul Ceremix ® 2X L |
| 4 hr | 0 | 0.75 | 0 | 0.81 |
| 23 hr | 0 | 3.24 | 0.35 | 5.70 |
| 74 hr | 0 | 5.49 | 0.85 | 7.13 |

EXAMPLE 6

The degradative ability of alginate lyase from *Bacillus stearothermophilus* strain W36-7-4 on alginate polymer produced by *Pseudomonas aeruginosa* (ATCC 9027).

1 ml of freshly grown *Pseudomonas aeruginosa* (ATCC 9027) suspension with OD at 660 nm of 0.43 was mixed with 5 mg and 10 mg alginate lyase lyophils and incubated at 37° C. for 30 minutes, 1 hour and 2 hours. The release of the unsaturated uronic acid moiety was monitored by absorbance at 230 nm as described above. The control was carried out under the identical conditions without enzyme addition. The results are tabulated in Table III.

TABLE III

| | $\Delta OD_{230\ nm}$ | | |
|---|---|---|---|
| Incubation time | 0 mg Enzyme | 5 mg Enzyme | 10 mg Enzyme |
| ½ hr | 0 | 0.15 | 0.245 |
| 1 hr | 0 | 0.27 | 0.51 |

TABLE III-continued

| | $\Delta OD_{230\,nm}$ | | |
|---|---|---|---|
| Incubation time | 0 mg Enzyme | 5 mg Enzyme | 10 mg Enzyme |
| 2 hr | 0 | 0.65 | 1.41 |

EXAMPLE 7

Effects of chemicals commonly used in water cooling systems on the activity of alginate lyase from *Bacillus stearothemophilus*.

EDTA (ethylene diamine tetraacetate), NaCl, $FeSO_4$, $NaAlO_2$, $Na_2MoO_4$, Zn, glutaraldehyde hydrazine and sodium nitrite were tested at the final concentration of 10 mM. Alginate lyase activity was monitored as described in Example 2 over 16 hours incubation. The results are summarized in Table IV. Alginate lyase from *Bacillus stearothermophilus* is demonstrated to be fairly stable in the presence of various oxidants, metal chelator, and salts which are commonly used in cooling water systems as antifoulants, biocides, coagulants/flocculants, corrosion inhibitors, etc.

TABLE IV

| Chemicals | Inhibition (%) of Chemicals on Enzyme Activity |
|---|---|
| EDTA | 0 |
| NaCl | 48.7 |
| $FeSO_4$ | 0 |
| $NaAlO_2$ | 0 |
| $Na_2MoO_4$ | 0 |
| Zn | 43.7 |
| glutaraldehyde | 0 |
| hydrazine | 0 |
| $NaNO_2$ | 0 |

I claim:
1. An isolated alginate lyase preparation comprising an alginate lyase produced by *Bacillus stearothermophilus* strain NRRL B-18394 and characterized by the ability to degrade algal cell wall and the alginate polymer produced by *Pseudomonas aeruginosa* said alginate lyase retaining 100% activity after four hours heat-treatment at 60° C.

2. A biologically pure culture of the *Bacillus stearothermophilus* strain NRRL B-18394, and mutants thereof characterized by the ability to produce an alginate lyase and by growth at pH 5.7, characterized also by having optimal temperature for growth at 55–60° C.

* * * * *